(12) United States Patent
Ajam et al.

(10) Patent No.: US 9,903,529 B2
(45) Date of Patent: Feb. 27, 2018

(54) FILTER HOLDER AND METHOD FOR STERILIZING THE FILTER HOLDER

(71) Applicant: Sartorius Stedim Biotech GmbH, Goettingen (DE)

(72) Inventors: Mohammed Saeed Ajam, Dortmund (DE); Jonas Mattern, Melsungen (DE); Jan Schaefer, Edermuende (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 99 days.

(21) Appl. No.: 14/366,509

(22) PCT Filed: Oct. 17, 2012

(86) PCT No.: PCT/EP2012/004337
§ 371 (c)(1),
(2) Date: Jun. 18, 2014

(87) PCT Pub. No.: WO2013/091747
PCT Pub. Date: Jun. 27, 2013

(65) Prior Publication Data
US 2015/0300557 A1    Oct. 22, 2015

(30) Foreign Application Priority Data

Dec. 19, 2011    (DE) .................. 10 2011 121 269

(51) Int. Cl.
*F16M 13/02*    (2006.01)
*A61L 2/07*    (2006.01)
(Continued)

(52) U.S. Cl.
CPC .............. *F16M 13/02* (2013.01); *A61L 2/07* (2013.01); *B01D 63/082* (2013.01); *B01D 65/00* (2013.01);
(Continued)

(58) Field of Classification Search
CPC .... F16M 13/02; F16M 13/801; F16M 13/601; F16M 1063/082601; F16M 2313/02;
(Continued)

(56) References Cited

U.S. PATENT DOCUMENTS 1,404,490 A * 1/1922 Stevenson ............... B30B 9/045
                                                      100/131
1,405,788 A * 2/1922 Komarek ................ B30B 11/16
                                                      425/237

(Continued)

FOREIGN PATENT DOCUMENTS

DE        3708733    10/1987
DE        3708734    10/1987
(Continued)

OTHER PUBLICATIONS

DE3708733A1 machine translation.*
(Continued)

*Primary Examiner* — David C Mellon
*Assistant Examiner* — Liam Royce
(74) *Attorney, Agent, or Firm* — Gerald E. Hespos; Michael J. Porco; Matthew T. Hespos (57) ABSTRACT

A filter holder for receiving filter cassettes (19) and a method for sterilizing the filter are provided. The filter holder has first and second parallel plates (3, 4). The first plate (3) is fixed and the second plate (4) is movable along at least one rail (2) by a drive (7, 9) so that the filter cassettes (19) can be clamped between the plates (3, 4) with a predefined clamping pressure. The drive (7, 9) is designed to be removable. The at least one rail (2) has at least one tension rod (5) with a spring clamping element (6) so that the first and second plates (3, 4) can be clamped with a pre-definable pressure against the filter cassettes (19).

13 Claims, 4 Drawing Sheets (51) Int. Cl.
*B01D 63/08* (2006.01)
*B01D 65/02* (2006.01)
*B01D 65/00* (2006.01)

(52) U.S. Cl.
CPC ........... *B01D 65/02* (2013.01); *B01D 65/022* (2013.01); *B01D 65/025* (2013.01); *B01D 2313/02* (2013.01); *B01D 2313/06* (2013.01); *B01D 2321/32* (2013.01)

(58) Field of Classification Search
CPC .. B01D 65/00; B01D 63/082; B01D 2313/06; B01D 2313/02; B01D 25/12; B01D 25/125; B01D 25/14; B01D 25/18; B01D 25/19; B01D 25/21; B01D 25/002; B01D 25/02; B01D 25/08; B01D 65/02; B01D 65/022; B01D 65/025; B01D 2321/32; B30B 9/06; A61L 2/07
See application file for complete search history.

(56) References Cited

U.S. PATENT DOCUMENTS

| | | | | | |
|---|---|---|---|---|---|
| 1,552,768 | A | * | 9/1925 | Smith | B30B 15/16 100/256 |
| 3,079,857 | A | * | 3/1963 | Vitali | B30B 9/045 100/113 |
| 3,875,040 | A | * | 4/1975 | Weltin | C25B 9/02 204/254 |
| 5,006,215 | A | * | 4/1991 | Borrione | B30B 7/026 204/253 |
| 5,194,148 | A | * | 3/1993 | Fresenius | B01D 25/19 100/197 |
| 5,510,025 | A | * | 4/1996 | Benesi | B01D 25/1275 210/227 |
| 2012/0111782 | A1 | | 5/2012 | Cirou et al. | |
| 2013/0306539 | A1 | | 11/2013 | Cirou et al. | |

FOREIGN PATENT DOCUMENTS

| | | |
|---|---|---|
| DE | 202004001955 | 6/2005 |
| WO | 2004113235 | 12/2004 |

OTHER PUBLICATIONS

English Translation of International Search Report PCT/EP2012/004337—dated Jun. 24, 2014.
International Search Report dated Jan. 1, 2013.
German Search Report dated Aug. 31, 2012.

* cited by examiner

FILTER HOLDER AND METHOD FOR STERILIZING THE FILTER HOLDER

BACKGROUND OF THE INVENTION

Field of the Invention

The invention concerns a filter holder for receiving filter cassettes having two plates which are movable relative to each other on at least one rail and between which the filter cassettes can be clamped, wherein a first plate is arranged so as to be fixed and a second, parallel plate is arranged so as to be movable, with a predefinable clamping pressure, by means of a drive. The invention further concerns a method for sterilizing a filter holder in an autoclave, with filter cassettes which are clamped between two plates that are movable relative to each other on at least one rail, wherein for sterilizing, the second movable plate is clamped against the first plate, which is fixedly connected to the rail, with a predefined tension rod pressure, by means of at least one tension rod arranged parallel to the rail and having a spring tensioning element, and the filter holder is autoclaved in the autoclave.

Description of the Related Art

The "SARTOFLOW®10 Stainless Steel Holder" company brochure discloses a filter holder for receiving filter cassettes with two plates that are movable relative to each other on parallel rails. The filter cassettes can be clamped between the plates. In this case, a first plate is fixedly arranged, and a second, parallel plate is arranged so as to be movable by means of a hydraulic drive with a predefinable clamping pressure. The hydraulic drive is designed as a hydraulic cylinder, which is arranged on a third plate fixedly connected to the rails. The hydraulic drive has a movable piston that moves the second movable plate in the direction of the first plate with a predefinable clamping pressure.

By using a hydraulic drive, the second plate can be moved with a high degree of precision and thus the predefined clamping force for moving the second plate, and thus the clamping pressure on the filter cassettes, can be precisely defined.

The disadvantage of such a basically tried and tested filter holder is that the filter holder cannot be autoclaved with the filter cassettes clamped in place. Because of the hydraulic fluid of the hydraulic drive, undesirable expansion would take place in the hydraulic cylinder, which would result in high clamping pressures or forces.

DE 37 08 733 C2 discloses a filter holder for receiving filter cassettes and has two plates movable relative to each other on a rail. The filter cassettes can be clamped between the plates. Here, a first plate and a second, parallel plate are movably arranged. Parallel to the rail, a tension rod having a spring tensioning element is provided by means of which rod the two plates can be connected to each other and clamped against the filter cassettes with a predefined tension rod pressure. The plates with the filter cassettes arranged in between them are manually joined together with a threaded connection by means of the tension rod. For the filtration process, the spring tensioning elements are blocked, and the clamping pressure with which the movable plate is pulled in the direction of the fixed plate is set manually by means of a torque wrench. To decrease the clamping pressure, the blocking of the spring tensioning element is cancelled by rotating the tension rod so that during the hot steam sterilizing process equalization can take place via the spring tensioning element. In this case, the advantage of hot steam sterilizing is offset by a certain lack of precision in the adjustment of the clamping pressure during the filtration process.

An object of the present invention is to improve the known filter holders such that, on the one hand, the pressure for clamping the plates with the filter cassettes arranged between them is adjustable with a high degree of precision by means of a drive while, on the other hand, the filter holder can be autoclaved with the filter cassettes clamped in place.

Another object is to provide a corresponding process for sterilizing the filter holders with filter cassettes.

SUMMARY OF THE INVENTION

The invention relates to a filter holder for receiving filter cassettes. The filter holder has two plates that are movable relative to each other on at least one rail, and filter cassettes can be clamped between the plates, with a first plate being fixedly arranged and a second, parallel plate being movably arranged by means of a drive having a predefinable clamping pressure. The drive is removable, and at least one tension rod having a spring tensioning element is provided parallel to the at least one rail. Thus, the two plates can be connected to each other and can be clamped against the filter cassettes with a predefinable tension rod pressure.

By using a drive for moving the second plate, the clamping pressure with which the filter cassettes are clamped in the filter holder can be predefined and precisely maintained. This is important for performing a filtration process. By additionally arranging a tension rod having a spring tensioning element, a predefinable tension rod pressure can be set which can be varied within certain limits by means of the spring tensioning element, thus preventing a pressure increase due to the expansion of the filter holder resulting from hot steam sterilization, as well as any related damage to the filter cassettes. In particular when using a hydraulic cylinder as a drive, autoclaving the hydraulic cylinder would result in an undesirable increase in pressure due to the expansion of the hydraulic fluid in the cylinder. After the filter cassettes have been clamped by means of the tension rod, which has a spring tensioning element, clamping by means of the drive can be released and the non-autoclavable drive can be removed. This will allow the filter holder with the clamped-in cassettes to be sterilized in an autoclave and/or with hot steam. The filter holder according to the invention thus allows steam-sterilizable filter cassettes to be sterilized in an autoclave and to be connected aseptically to an already sterile "single-use package." In this case, a single-use package is to be understood as, for example, a system comprised of a recirculation container and a filtrate container with corresponding connecting hoses which can be connected to form an overall system with the filter holder with filter cassettes. All parts of the overall system package, with the exception of the filter holder without filter cassettes, can be designed as single-use parts. In addition, the filter holder with the filter cassettes can again be autoclaved after a filtration process and thus be used for detoxification.

According to a preferred embodiment of the invention, a third plate is arranged offset from the second plate on the side of the latter facing away from the first plate, which third plate is fixedly connected to the at least one rail, and the removable drive is fixedly attachable to the third plate. The drive can be easily mounted on and removed from the third plate, e.g. by means of a locking device or a threaded connection.

According to another preferred embodiment of the invention, the drive is designed as a pressurizable hydraulic cylinder by means of whose movable piston the second plate can be clamped against the filter cassettes with the pre-defined clamping pressure. The hydraulic cylinder can be connected to a pump by means of a hydraulic line with, preferably, a pressure gauge being arranged between pump and hydraulic cylinder. In this case, the pump can, in particular, also be designed as a manual pump.

According to another preferred embodiment of the invention, four rails are provided on which the second plate is movable relative to the first plate. In particular by using three or four rails, parallelism between the plates is ensured, and this is required for even application of pressure on the filter cassettes to be clamped between the plates.

According to another preferred embodiment of the invention, two tension rods each having one spring tensioning element are provided by means of which the two plates can be connected and clamped against the filter cassettes with the predefinable tension force. In this case, the filter holder—without the drive—can be autoclaved with the filter cassettes which have been pretensioned by means of the tension rods fitted with spring tensioning elements.

The invention also relates to a method for sterilizing a filter holder in an autoclave with filter cassettes. The filter cassettes are clamped between two plates that are movable relative to each other on at least one rail. For sterilizing purposes, the second movable plate is clamped by at least one tensioning rod that has a spring tensioning element arranged parallel to the rail. More particularly, the second movable plate is clamped against the first plate, which is connected fixedly to the rail. The filter holder then is autoclaved in the autoclave. The method further includes—after autoclaving—fixedly connecting a drive to the rail for the filtration process. The drive clamps the second plate against the first plate with a predefined clamping pressure, and the tension rod is released by the spring tensioning element.

By using a tension rod having a spring tensioning element, the filter holder with the clamped-in filter cassettes can be sterilized by means of hot steam in an autoclave.

After autoclaving, a drive can be fixedly attached to the rail, said drive clamping the second plate against the first plate with a relatively high degree of precision using pre-defined force or clamping pressure. Then the tension rod can be released by means of the spring tensioning element.

On the one hand, this allows the filter holder with cassettes to be autoclaved, and on the other hand they can be precisely clamped with a predefinable force or pressure for the filtration process. Due to the fact that the tension rod is not released by means of the spring tensioning element until clamping pressure is applied to the second plate by means of the drive, leaks are prevented between the process steps.

According to a preferred embodiment of the invention, the tension rod pressure used for clamping the plates for the sterilization process is lower than the clamping pressure used for clamping the plates during the filtration process. This ensures that during autoclaving, the pressure on the plates remains in a predefined range and that the filter cassettes are sealed in a relatively protective manner during the autoclaving process.

According to another preferred embodiment of the invention, the drive has a hydraulic cylinder which is removably mounted on or fixedly connected to a third plate, which is arranged offset from the second plate and is connected to the rail, in such a manner that the movable piston of the cylinder applies the necessary clamping pressure to the second plate, thus clamping the filter cassettes. The hydraulic cylinder of the drive can be easily mounted on the third plate and securely attached to the latter, such that its movable piston can apply the necessary force to the second plate for clamping the filter cassettes.

According to another preferred embodiment of the invention, the drive is mounted for carrying out autoclaving and a reduced clamping pressure corresponding to the tension rod pressure is applied to the second plate, and subsequently the tension rod is tightened and the plates are clamped with the predefined tension rod pressure by means of the spring tensioning element. Then the drive is released and removed and, after autoclaving, the drive is re-attached and the clamping pressure provided for the filtration process is set, whereupon the tension rod is released. Such a procedure ensures that the filter cassettes are always sufficiently clamped, specifically in between the process steps According to another preferred embodiment of the invention, the filter holder is autoclaved with a hose set attached to the filter cassettes, and then it is integrated aseptically into an already sterile process workflow.

Additional details of the invention can be obtained from the detailed description below and from the attached drawings, which show preferred exemplary embodiments of the invention.

DETAILED DESCRIPTION OF THE ILLUSTRATED EMBODIMENTS

A filter holder 1 essentially comprises rails 2, plates 3, 4, tension rods 5, spring tensioning elements 6, and a drive 7.

Figure 1:
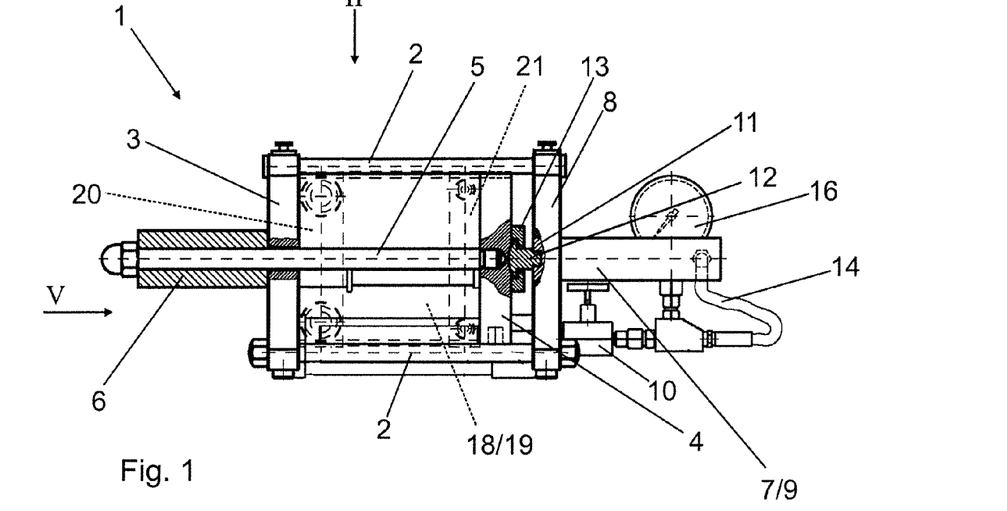
FIG. 1 is a partially cross-sectional side view of a filter holder, with broken lines indicating a filter cassette stack delimited by adapter plates.
Figure 2:
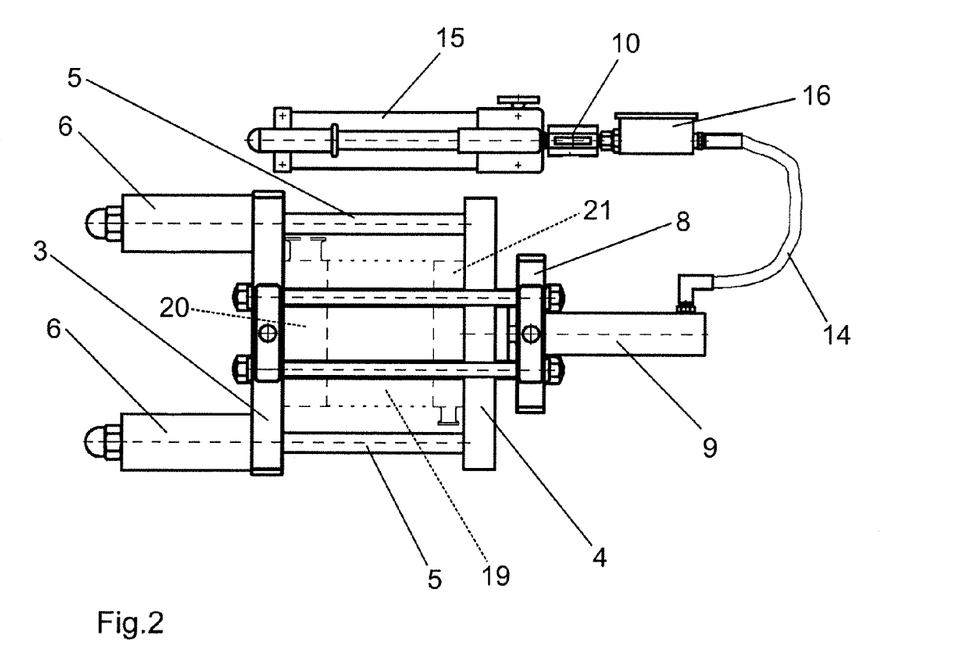
FIG. 2 is a top view of the filter holder of FIG. 1 as viewed from Direction II.
Figure 5:
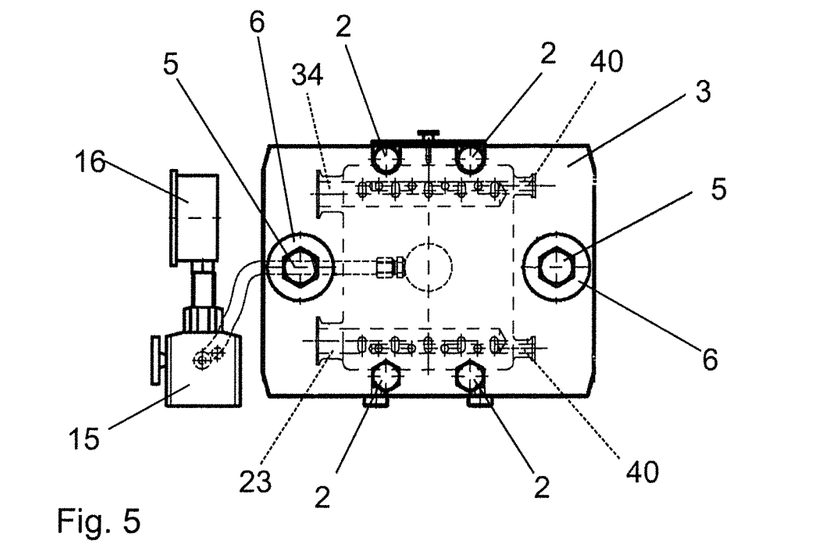
FIG. 5 is a side view of the filter holder from FIG. 1 as viewed from Direction V.

According to the exemplary embodiment in FIGS. 1, 2, and 5, four rails 2 are fixedly attached to the first plate 3. The second plate 4 is movably guided on each of rails 2. A third plate 8 is arranged offset from the second plate 4 on the side of the latter facing away from the first plate 3, said third plate being also fixedly connected to the rails 2. The drive 7 is removably arranged on the third plate 8. The drive 7 is comprised of a pressurizable hydraulic cylinder 9 having a male thread, by means of which it can be fixedly screwed into an opening in the third plate 8 which has a female thread. The hydraulic cylinder 9 has a movable piston 11 which, by means of a pressure component 12, applies a clamping pressure on the movable second plate 4. The pressure component 12 is connected to the second plate 4 by means of a ring 13. Via a hydraulic line 14, the hydraulic cylinder 9 is connected to a pump 15, which is designed as a manual pump in the exemplary embodiments. Between the pump 15 and the hydraulic cylinder 9, a pressure gauge 16 is arranged for indicating the pressure in the hydraulic cylinder 9. Between the pump 15 and the pressure gauge 16, a needle valve 10 can be arranged.

The first plate 3 and the second plate 4 are additionally connected to each other by means of two tension rods 5. In this case, each of the tension rods 5 has a spring tensioning element 6. By means of the tension rods 5, the plates 3, 4 can be clamped in relation to each other by means of a tension rod pressure exerted by spring tensioning elements 6, the pressure being predefined by compression springs that are not shown here.

Figure 3:
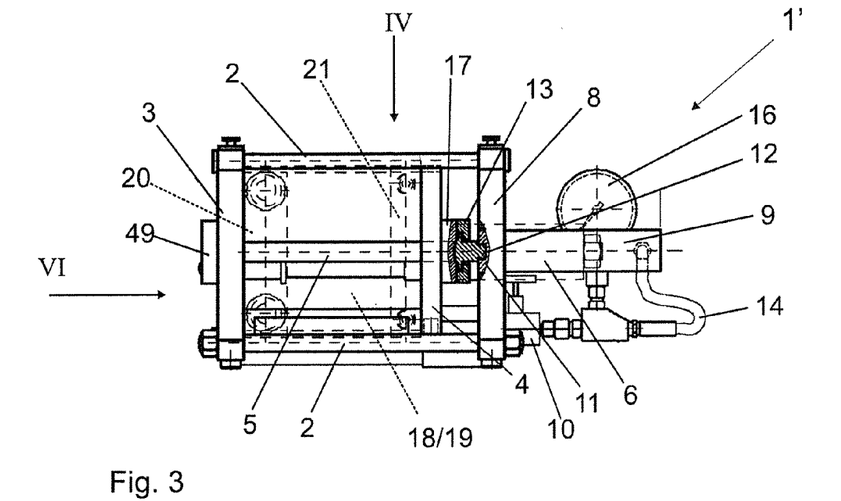
FIG. 3 is a partially cross-sectional side view of another filter holder, with broken lines indicating a filter cassette stack delimited by adapter plates.
Figure 4:
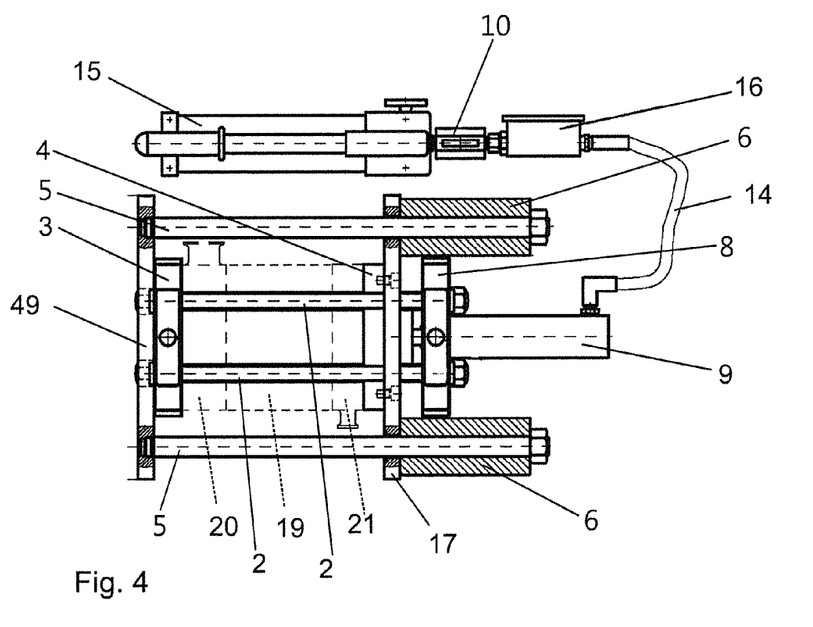
FIG. 4 is a top view of the filter holder from FIG. 3 as viewed from Direction IV.
Figure 6:
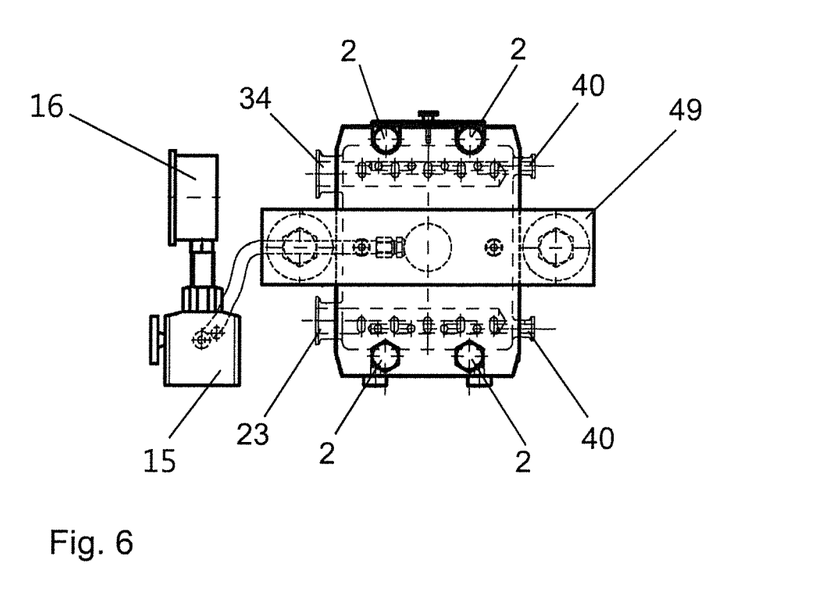
FIG. 6 is a side view of the filter holder from FIG. 3 as viewed from Direction VI.

According to the exemplary embodiment in FIGS. 1, 2, and 5, tension rods 5 with their spring tensioning elements 6 are arranged offset from the first plate 3. According to the exemplary embodiments in FIGS. 3, 4, and 6, the tension rods 5 with their spring tensioning elements 6 are arranged offset from the movable second plate 4 by means of a first cross member 17, which is bolted to the second plate 4. A second cross member 49 is bolted to the first plate 3 and receives the ends of the tension rods 5.

A cassette stack 18 can be clamped between the plates 3, 4, said cassette stack having a plurality of filter cassettes 19 and also having a filter plate 20, 21 at each end facing the plates 3, 4, with the first filter plate 20 adjacent to first plate 3 being designed as a feed plate/retentate plate distributing the fluid to be filtered, and the second filter plate 21 being designed as a permeate plate collecting the permeate.

By means of the drive 7, the filter cassettes 19 and filter plates 20, 21 can be clamped between plates 3, 4 with a predefined clamping pressure. At the same time or separately, the filter cassettes 19 and filter plates 20, 21 can be clamped via the tension rods 5 and spring tensioning elements 6 with a predefinable tension rod pressure, which is lower than the clamping pressure.

Figure 7:
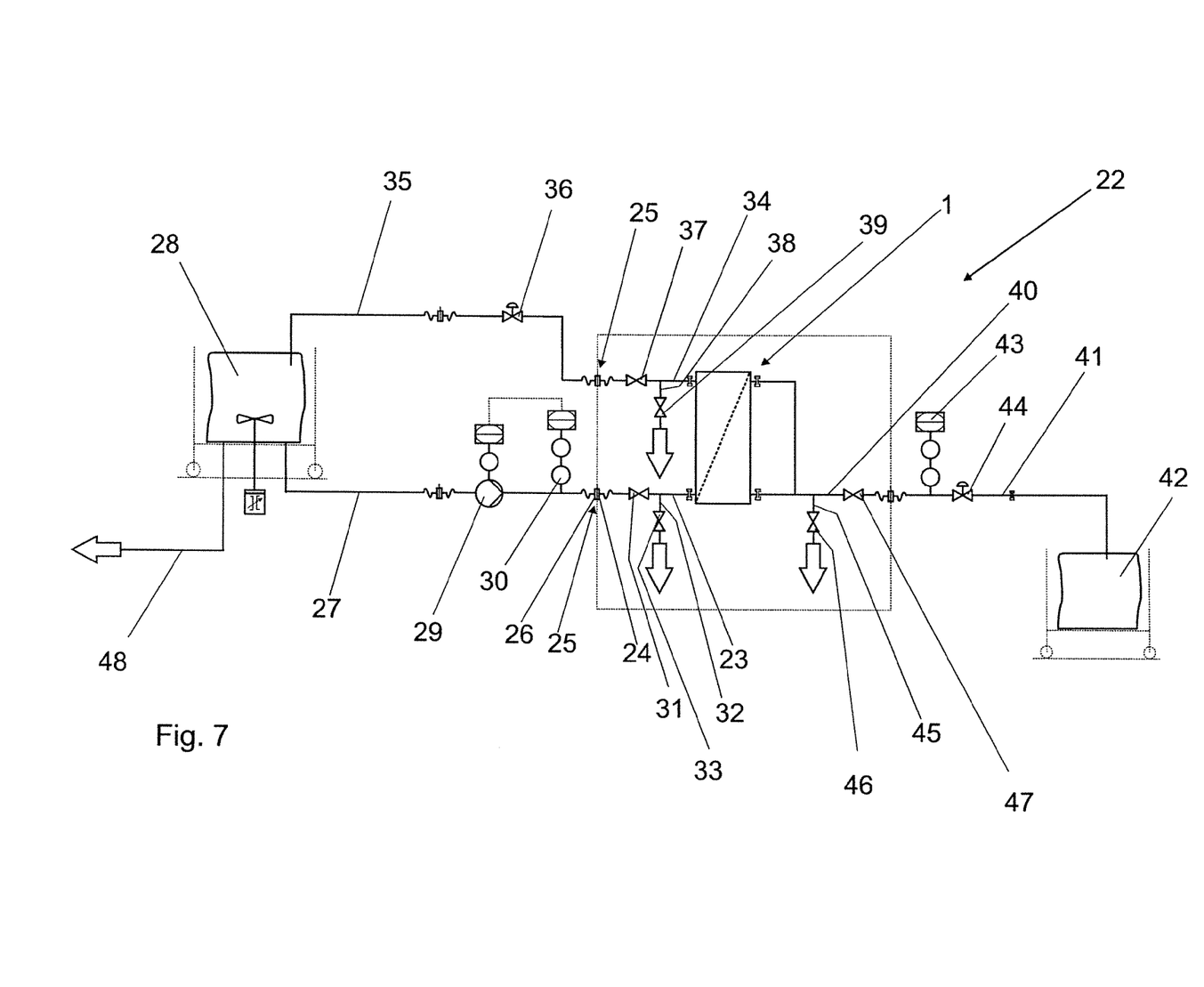
FIG. 7 is a schematic drawing of an overall system with a filter cassette stack connected.

The filter holder 1, which with its cassette stack 18 is sterilizable in an autoclave, can be integrated aseptically into a sterile overall system 22 which is designed as a single-use system. For this purpose, the first filter plate 20 has a feed line 23 having a first part 24 of a sterile connector 25 which is connectable to a second part 26 of the sterile connector 25. The second part 26 is arranged on a drain line 27 of a recirculation container 28. In addition, a recirculation pump 29 is arranged in the drain line 27 and a pressure gauge 30 for measuring the feed pressure is arranged downstream of the recirculation pump in the direction of filter holder 1. The recirculation pump 29 can be controlled by means of the pressure gauge 30. A valve 31 is arranged in the feed line 23 of the filter holder 1 or of the cassette stack 18, respectively. For autoclaving, the feed line 23 has a connecting line 32 to a glass beaker, which is not shown here, said line being closable by means of a valve 33.

The first filter plate 20 has a retentate line 34, which also connects the first filter plate 20 to the recirculation container 28 by means of a sterile connector 25 having a recirculation line 35 so that retentate from the cassette stack 18 can be returned to the recirculation container 28. In the recirculation line 35, a control valve 36 is arranged in an essentially known manner. Between the first filter plate 20 and the sterile connector 25, a valve 37 is arranged in retentate line 35. The recirculation line 35 also has a connecting line 38 which can also be connected with a glass beaker by means of a valve 39 for autoclaving.

The second filter plate 21 of the cassette stack 18 has a permeate line 40 which is connected by a sterile connector 25 to a feed line 41 of a filtrate or permeate container 42. A pressure sensor 43 and a control valve 44 are arranged in feed line 41 to the permeate container 42.

For autoclaving, the permeate line 40 has a connecting line 45 to a glass beaker, said line being closable by means of a valve 46. In the permeate line 40, a valve 47 is arranged upstream from the sterile connector 25.

Recirculation container 28 has a second drain line 48 to a harvesting container which is not shown here.

For autoclaving the filter holder 1, the drive 7, i.e. the hydraulic cylinder 9, is mounted on the third plate 8 and fixedly connected thereto, e.g. by means of a male thread. The cassette stack 18 with the filter cassettes 19 and both filter plates 20, 21 are inserted between the plates 3, 4, with the second plate 4 being moved in the direction of the first plate 3 by means of the piston 11 of the hydraulic cylinder using a reduced clamping pressure which corresponds to the tension rod pressure, so that cassette stack 18 is clamped with the reduced clamping pressure. Then, the tension rods are tightened and plates 3, 4 are clamped with the predefined tension rod pressure by means of spring tensioning elements 6. Next, the piston 11 is refracted and the hydraulic cylinder 9, with the piston 11, is removed from the third plate 8, and the filter holder 1 is sterilized by means of hot steam in an autoclave that is not shown here. After sterilizing or autoclaving, the hydraulic cylinder 9 is again mounted onto the third plate 8, and the clamping pressure predefined for the filtration process is set, whereupon the tension rods 5 are released again. Now the autoclaved filter holder with the cassette stack 18 can be inserted into the overall system by means of the sterile connector 25.

Of course the embodiments discussed in the specific description and shown in the Figures are only illustrative exemplary embodiments of the present invention. In the light of the disclosure made here, a person skilled in the art is provided with a wide range of options for variations.

LIST OF REFERENCE NUMBERS

1 Filter holder
2 Rails
3 First plate
4 Second plate
5 Tension rods
6 Spring tensioning elements
7 Drive
8 Third plate
9 Hydraulic cylinder
10 Needle valve
11 Piston of 9
12 Pressure component
13 Ring
14 Hydraulic line
15 Pump
16 Pressure gauge
17 Cross member
18 Cassette stack
19 Filter cassettes
20 Filter plate
21 Filter plate
22 Overall system
23 Feed line from 20
24 First part of 5
25 Sterile connector
26 Second part of 5
27 Drain line
28 Recirculation container
29 Recirculation pump
30 Pressure gauge
31 Valve 32 Connecting line of 23
33 Valve
34 Retentate line
35 Recirculation line
36 Control valve
37 Valve of 34
38 Connecting line of 24
39 Valve of 38
40 Permeate line
41 Feed line of 42
42 Permeate container
43 Pressure sensor
44 Control valve
45 Connecting line
46 Valve of 45
47 Valve of 40
48 Second drain line of 28
49 Second cross member of 3

The invention claimed is:

1. A filter holder (1), comprising:
at least one rail (2);
first, second and third parallel plates (3, 4, 8), the first and third parallel plates (3, 8) being fixed on the at least one rail (2), and spaced from one another, the second parallel plate (4) being between the first and third parallel plates (3, 8) and being movable relative to the at least one rail (2) and relative to the first and third parallel plates (3, 8);
a drive (7) that is removably attached by a locking device or a threaded connection to a side of the third parallel plate (8) facing away from the first and second parallel plates (3, 4), the drive (7) being operable for moving the second parallel plate (4) toward and away from the first parallel plate (3) and for generating a predefinable clamping pressure; and
at least one tension rod (5) parallel with the at least one rail (2) and having a spring tensioning element (6) attached on a side of the first parallel plate (3) facing away from the second and third parallel plates (4, 8), the at least one tension rod (5) connecting the first and second parallel plates (3, 4) to each other and being configured for generating a predefined tension rod pressure on the first and second parallel plates exerted by the spring tensioning element (6), whereby filter cassettes (19) can be clamped between the first and second parallel plates (3, 4) at the predefined tension rod pressure when the drive (7) is removed.

2. The filter holder of claim 1, further comprising:
a cassette stack (18) having a plurality of the filter cassettes (19) in a stacked array and first and second filter plates (20, 21) at opposite ends of the stacked array of the filter cassettes (19), the cassette stack (18) being disposed to so that the first filter plate (20) faces the first parallel plate (3) of the filter holder (1) and the second filter plate (21) faces the second parallel plate (4) of the filter holder (1), the first filter plate (20) defining a feed plate or a retentate that is configured for distributing fluid that is to be filtered.

3. The filter holder of claim 1, wherein
the drive (7) comprises a pressurizable hydraulic cylinder (9) that comprises a movable piston (11) configured to move the second parallel plate (4) toward the first parallel plate (3) with the predefined clamping pressure.

4. The filter holder of claim 3, wherein
the hydraulic cylinder (9) is connected to a pump (15) by a hydraulic line (14) and a pressure gauge (16) is arranged between the pump (15) and the hydraulic cylinder (9).

5. The filter holder of claim 1, wherein
the at least one rail (2) comprises four rails (2) on which the second parallel plate (4) is movable relative to the first parallel plate (3).

6. The filter holder of claim 1, wherein
the at least one tension rod (5) comprises two tension rods (5) each having one spring tensioning element (6), the tension rods (5) connecting the first and second parallel plates (3, 4) to each other and being configured to generate the predefinable tension rod pressure.

7. The filter holder of claim 1, wherein
the filter holder (1) is autoclavable when the drive (7) is removed.

8. An autoclavable filter assembly, comprising:
a cassette stack (18) having a plurality of the filter cassettes (19) in a stacked array; and
a filter holder (1) for holding the cassette stack (18), the filter holder (1) including:
at least one rail (2);
first, second and third parallel plates (3, 4, 8), the first and third parallel plates (3, 8) being fixed on the at least one rail (2), the second parallel plate (4) being between the first and third parallel plates (3, 8) and being movable relative to the at least one rail (2) and relative to the first and third parallel plates (3, 8) with the cassette stack (19) being between the first and second parallel plates (3, 4);
a drive (7) that is removably attached by a locking device or a threaded connection to a side of the third parallel plate (8) facing away from the first and second parallel plates (3, 4), the drive (7) being configured for moving the second parallel plate (4) toward and away from the first parallel plate (3) and for generating a predefinable clamping pressure on the cassette stack (18); and
at least one tension rod (5) parallel with the at least one rail (2) and connecting the first and second parallel plates (3, 4) to each other, the at least one tension rod (5) having a spring tensioning element (6) attached on a side of the first parallel plate (3) facing away from the second and third parallel plates (4, 8) and clamping the first and second parallel plates (3, 4) against the cassette stack (18) independent of the drive (7) and with a predefined tension rod pressure exerted by the spring tensioning element (6), whereby the drive (7) can be removed so that remaining parts of the filter assembly can be autoclaved.

9. The filter assembly of claim 8, wherein the cassette stack (18) further comprises first and second filter plates (20, 21) at opposite ends of the stacked array of the filter cassettes (19), the cassette stack (18) being disposed to so that the first filter plate (20) faces the first parallel plate (3) of the filter holder (1) and the second filter plate (21) faces the second parallel plate (4) of the filter holder (1), the first filter plate (20) defining a feed plate or a retentate that is configured for distributing a fluid that is to be filtered.

10. The filter assembly of claim 8, wherein the drive (7) comprises a pressurizable hydraulic cylinder (9) that comprises a movable piston (11) configured to clamp the second parallel plate (4) against the filter cassettes (19) with the predefined clamping pressure.

11. The filter assembly of claim 10, wherein the hydraulic cylinder (9) is connected to the pump (15) by a hydraulic line (14) and a pressure gauge (16) is arranged between a pump (15) and the hydraulic cylinder (9).

12. The filter assembly of claim 8, wherein the at least one rail (2) comprises four rails (2) on which the second parallel plate (4) is movable relative to the first parallel plate (3).

13. The filter holder of claim 8, wherein the at least one tension rod (5) comprises two tension rods (5) each having one spring tensioning element (6), the tension rods (5) enabling the first and second parallel plates (3, 4) to be connected to each other and clamped against the filter cassettes (19) with the predefinable tension rod pressure.

* * * * *